United States Patent [19]

Heidgen

[11] Patent Number: Plant 6,355

[45] Date of Patent: Oct. 25, 1988

[54] GERANIUM NAMED WATERMELON DELIGHT

[76] Inventor: Charles F. Heidgen, 821 Walnut St., Batavia, Ill. 60510

[21] Appl. No.: 782,736

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Watermelon Delight, characterized by its cascading growth habit; its watermelon pink, medium-sized flowers; its lightly zoned medium to dark green foliage; its continuous blooming habit and its heat tolerance.

1 Drawing Sheet

The present discovery, hereinafter referred to by the cultivar name, Watermelon Delight, relates to a new and distinct geranium plant.

BACKGROUND

Watermelon Delight is a new and improved variety which has resulted from definite breeding programs and experiments carried on by me in my greenhouses at 821 Walnut St., Batavia, Ill. Our experiments commenced in March, 1977 and are being carried on continuously. This seedling, 79×018C, resulted from a cross between Deacon Lilac Mist, an unpatented, floribunda zonal geranium and Fraicheur, an unpatented, standard zonal geranium.

Asexual reproduction of Watermelon Delight has been accomplished from vegetative cuttings in my greenhouse in Batavia, Ill. Examination of the plants so propagated has demonstrated that the combination of characteristics herein disclosed for Watermelon Delight are firmly fixed and retained through successive generations of asexual reproduction.

SUMMARY

The new and patentable characteristics of Watermelon Delight reside in its cascading growth habit, its medium-sized, watermelon pink colored flowers, its continuous flowering habit, its medium to dark green, lightly zoned foliage and its heat tolerance.

DESCRIPTION OF DRAWING

The photograph shows the plant and flower of a fully developed geranium of the new variety, Watermelon Delight.

BOTANIC DESCRIPTION

The Plant

Growth: Watermelon Delight is a continuous bloomer with a very distinctive watemelon pink colored flower. The flower head (truss) is medium-sized and quite resistant to shattering. It has a cascading growth habit. It has a vigorous growth rate producing a typical 10" flowering basket in 10–12 weeks from four 2¼ inch plants using standard commercial culture. This geranium is also known to be ethrel responsive.

Blooming habit: Always a continuous bloomer, throughout the year, outdoors or in the greenhouse. A mature 10" basket would commonly produce 15–25 heads at one time and it is quite heat tolerant.

Inflorescence: Medium-sized head, rounded, measuring 3¼–4 inches in diameter.

Foliage:

*Quantity.*—Abundant.

*Size.*—Medium, 1¾–2½ inches across.

*Color.*—Spinach Green(0960/2) with Parsley Green(00962/3) zone. (The Royal Horticultural Society Horticultural Colour Chart).

*Texture.*—Slightly pubescent upper and lower surface.

Stem: Medium, normal internodes, somewhat upright, but procumbent growth habit.

Petiole: Medium length, 1¾–2¼ inches, same color as leaf.

The Flower

Truss:

*Size.*—Medium-size, 3¼–4 inches in diameter.

*Shape.*—Round, a globe as it opens.

*Number of Florets.*—Variable, range from 20–42, average 25–35.

*Lasting quality.*—Average to longer than average. Blooms remain 6–13 days, longer if cool and dry.

Bud:

*Sepals.*—Short, pointed.

*Color.*—Claret Rose(021)The Royal Horticultural Society Horticultural Colour Chart).

*Form.*—Rounded.

Florets:

*Size.*—1¼ to 1⅜ inches across.

*Petalage,*—Double, 10–15.

*Color.*—Geranium Lake(20/2)(The Royal Horticultural Society Horticultural Colour Chart).

Form: Very double, petals range from½ to ¾ inch wide.

Lasting quality: Average to longer than average. Floret lasts 4–9 days, the truss lasts 10–13 days.

Behavior: This plant, when blooming, has medium-sized, watermelon pink blooms that are beautiful against the medium to dark green, lightly zoned, medium-sized foliage.

Having thus disclosed my invention, I claim:

1. A new and distinct variety of geranium plant, substantially as shown and described, characterized by its cascading growth habit, its watermelon pink, medium-sized flowers, its lightly zoned medium to dark green foliage, its continuous blooming habit and its heat tolerance.

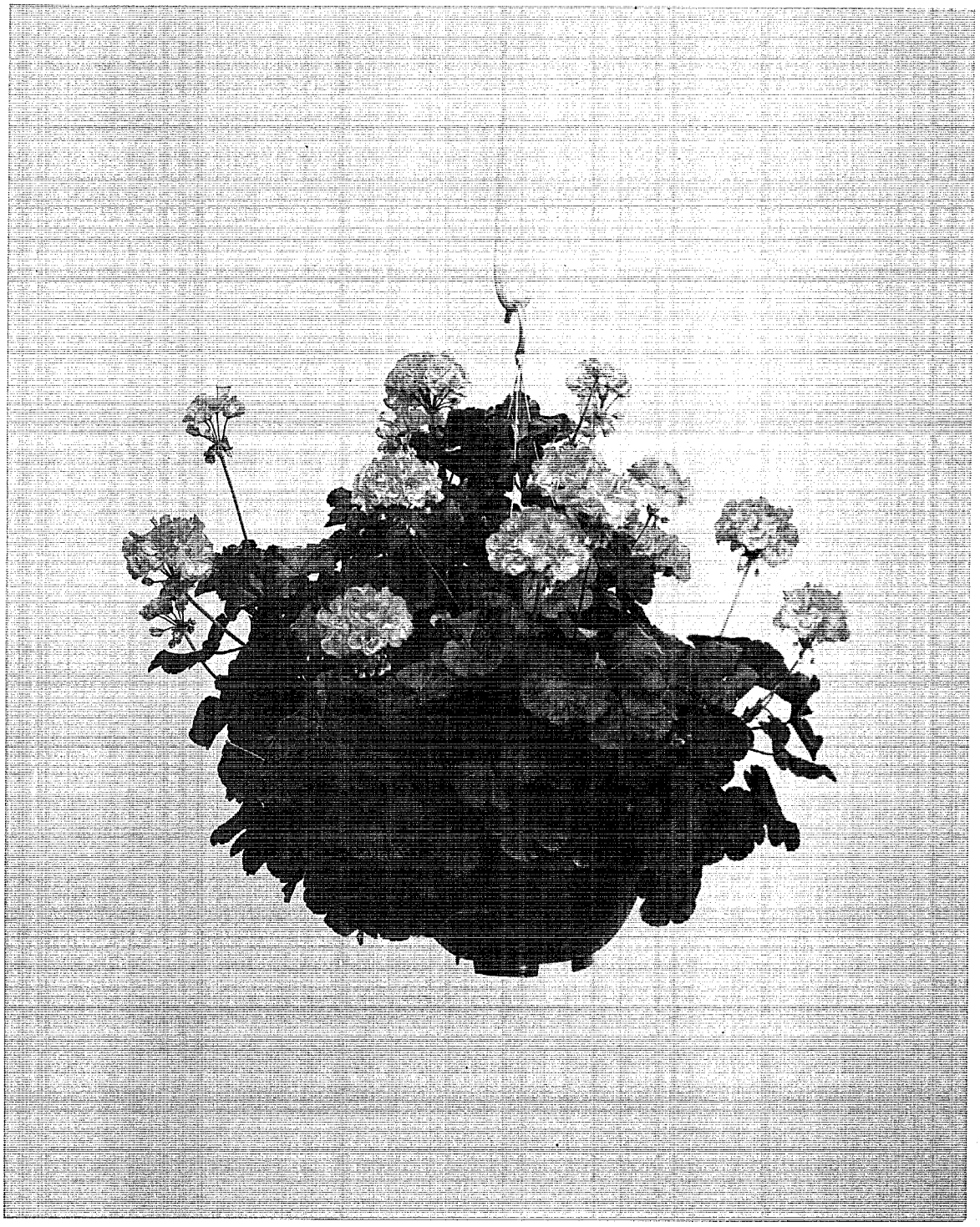

* * * * *